United States Patent [19]

Clark et al.

[11] Patent Number: 5,574,158

[45] Date of Patent: Nov. 12, 1996

[54] COMPOUNDS

[75] Inventors: Barry P. Clark, Lower Froyle; John R. Harris, Guildford, both of United Kingdom

[73] Assignee: Lilly Industries Limited, Basingstoke, England

[21] Appl. No.: 603,829

[22] Filed: Feb. 20, 1996

Related U.S. Application Data

[62] Division of Ser. No. 347,546, Nov. 30, 1994.

[30] Foreign Application Priority Data

Dec. 3, 1993 [GB] United Kingdom .................. 9324871

[51] Int. Cl.$^6$ .............................................. C07D 273/08
[52] U.S. Cl. ........................ 540/469; 540/450; 540/467; 540/468
[58] Field of Search .................... 540/450, 467, 540/468, 469

[56] References Cited

U.S. PATENT DOCUMENTS

| | | | |
|---|---|---|---|
| 4,076,724 | 2/1978 | Lehn ...................... | 540/469 |
| 4,843,158 | 6/1989 | Smith ..................... | 540/469 |
| 5,187,103 | 2/1993 | Czech et al. ............. | 540/469 |

Primary Examiner—Mukund J. Shah
Assistant Examiner—Pavanaram K. Sripada
Attorney, Agent, or Firm—MaCharri R. Vorndran-Jones; David E. Boone

[57] ABSTRACT

A compound of the formula:

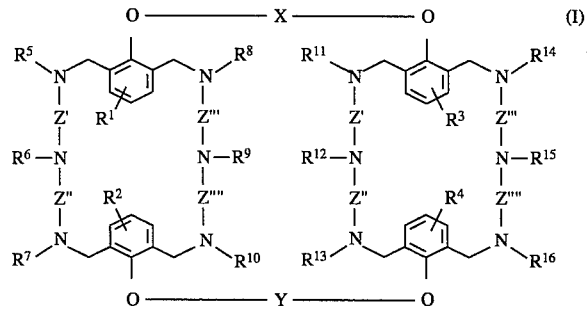

in which each $R^1$ to $R^4$ group is hydrogen, $C_{1-4}$ alkyl, $C_{1-4}$ alkoxy, $C_{1-4}$ alkoxy-carbonyl, halo, hydroxy, nitro, cyano, trihalomethyl or optionally substituted phenyl, each $R^5$ to $R^{16}$ group is hydrogen or $C_{1-4}$ alkyl, each Z', Z", Z''' and Z'''' group is an alkylene radical, and X and Y are each $-(CH_2)_n-$ or $-(CH_2)_m-A-(CH_2)_p-$ where A is $-CH=CH-$, optionally substituted phenylene or optionally substituted naphthalenyl, n is 2 to 10, and m and p are each 1 or 2, salts thereof, and intermediates for the production thereof.

2 Claims, No Drawings

COMPOUNDS

This application is a division of application Ser. No. 08/347,546 filed Nov. 30, 1994 now pending.

This invention relates to novel compounds and their use. The compounds of the invention have the formula:

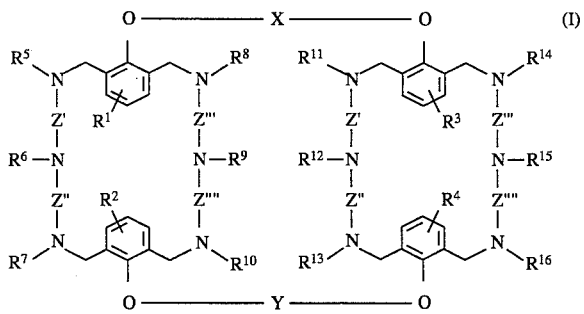  (I)

in which each $R^1$ to $R^4$ group is hydrogen, $C_{1-4}$ alkyl, $C_{1-4}$ alkoxy, $C_{1-4}$ alkoxyl-carbonyl, halo, hydroxy, nitro, cyano, trihalomethyl or optionally substituted phenyl, each $R^5$ to $R^{16}$ group is hydrogen or $C_{1-4}$ alkyl, each $Z'$, $Z''$, $Z'''$ and $Z''''$ group is an alkylene radical, and X and Y are each $-(CH_2)_n-$ or $-(CH_2)_m-A-(CH_2)_p-$ where A is $-CH=CH-$, optionally substituted phenylene or optionally substituted naphthalenyl, n is 2 to 10, and m and p are each 1 or 2; and salts thereof.

Compounds of the invention in which $R^5$ to $R^{16}$ are hydrogen are indicated for use in the treatment of diseases of the central nervous system. Such compounds and those in which $R^5$ to $R^{16}$ take values other than hydrogen, are also of use as chelating agents as for example with metal cations such as lead and zinc, and transition metal cations, for example, lanthanum, uranium, gold and especially copper, iron and cobalt.

When reference is made to $C_{1-4}$ alkyl in the above formula, preferred groups are methyl, ethyl, propyl, isopropyl and tert. butyl. Especially preferred groups are methyl and ethyl. A $C_{1-4}$ alkoxy group is one such alkyl group linked via an oxygen atom. Preferred halo groups are fluoro, chloro and bromo, and trifluoromethyl is the preferred example of trihalomethyl.

An $R^1$ to $R^4$ group is preferably hydrogen, $C_{1-4}$ alkyl, $C_{1-4}$ alkoxy, halo, hydroxy, nitro, cyano, trihalomethyl or optionally substituted phenyl, and especially hydrogen, halo, $C_{1-4}$ alkyl or $C_{1-4}$ alkoxy.

An optionally substituted phenyl or naphthalenyl group is preferably unsubstituted phenyl or naphthalenyl, and can also be phenyl or naphthalenyl substituted with one or more substituents, preferably one or two substituents selected from halo, preferably fluoro, chloro or bromo, trifluoromethyl, $C_{1-4}$ alkoxy, hydroxy, nitro, $C_{1-4}$ alkyl, $C_{1-4}$ alkylthio and carboxy. An A radical is preferably of the form:

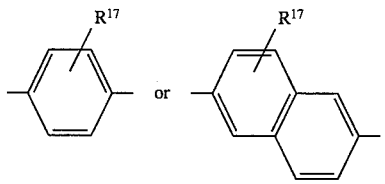

where $R^{17}$ is a substituent, for example one such listed above, that is attached at any position on the phenylene or naphthalenyl nucleus.

The X and Y groups are preferably $-(CH_2)_4-$, $-(CH_2)_6-$,

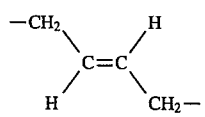

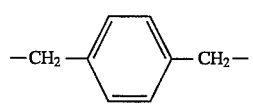

and

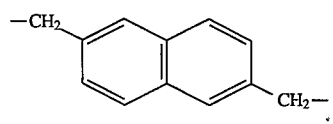

The radicals $Z'$ to $Z''''$ in the above general formula are alkylene groups which are each preferably of the formula $-CH_2(CR'R'')_sCH_2-$ where R' and R'' are each hydrogen or $C_{1-4}$ alkyl and s is 0, 1 or 2. More preferably the alkylene group is $-(CH_2)_t-$ where t is 2 to 4, and $Z'$ to $Z''''$ are identical.

Thus, a preferred group of compounds according to the invention is one of the formula:

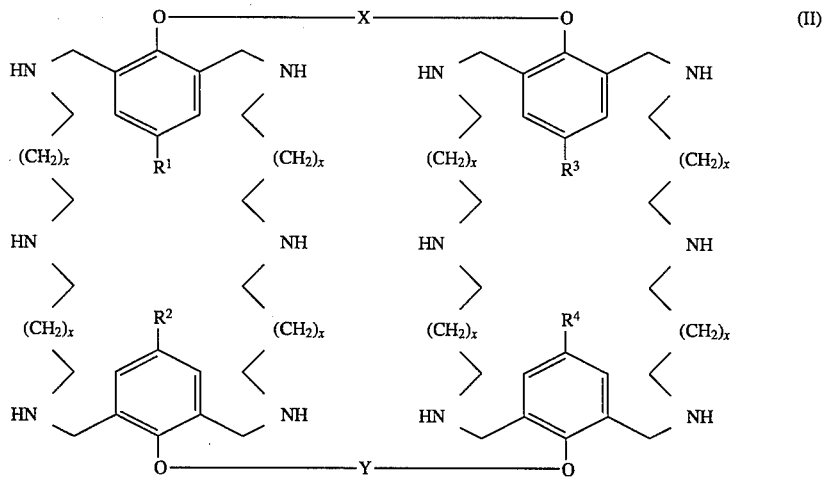  (II)

in which $R^1$ to $R^4$ are each hydrogen, halo, $C_{1-4}$ alkyl or $C_{1-4}$ alkoxy, x is 0, 1 or 2, X and Y are —$(CH_2)_n$— where n is 2 to 10, or

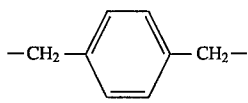

and salts thereof.

It will be understood that salts of the compounds of the invention can be prepared, and such salts are included in the invention. They can be any of the well known acid or base addition salts. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicyclic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts or are useful for identification, characterisation or purification. Furthermore, salts that are not satisfactory for pharmaceutical purposes may, of course, be of practical use as chelating agents in another context.

It will be appreciated that the compounds of the invention can contain one or more asymmetric carbon atoms which give rise to isomers. The compounds are normally prepared as racemic mixtures and can conveniently be used as such, but individual isomers can be isolated by conventional techniques if so desired. Such racemic mixtures and isomers are included in the invention.

The invention also includes a process for producing compounds of formula I above, which comprises (1) reducing a compound of the formula:

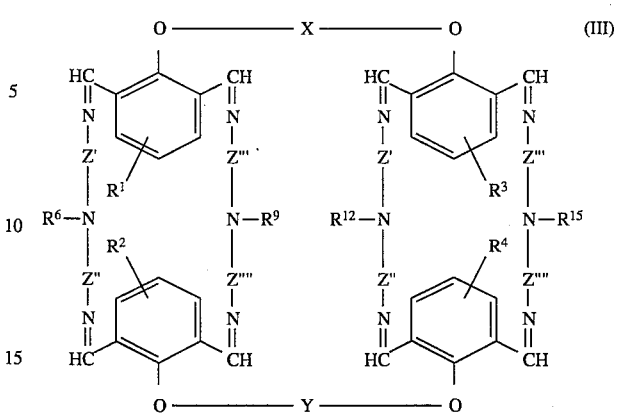

to give a compound of formula I in which $R^5$, $R^7$, $R^8$, $R^{10}$, $R^{11}$, $R^{13}$, $R^{14}$ and $R^{16}$ are hydrogen, or (2) alkylating a compound of formula I in which one or more of $R^5$ to $R^{16}$ is hydrogen.

Intermediates of formula III, and salts thereof, are novel compounds. Those in which $R^6$, $R^9$, $R^{12}$ and $R^{15}$ are hydrogen can exist as an imine-aminal, such as for example:

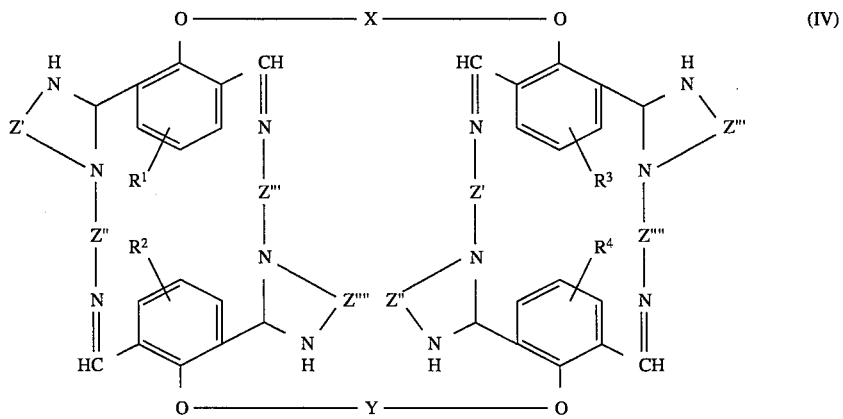

also optionally in salt form.

Compounds of formula III and IV are useful chelating agents in addition to their function as intermediates for the production of compounds of the formula I. They can exist as an equilibrium between formula III and IV in solution and can be isolated as compounds of formula IV in solid, crystalline, form. Both forms can be utilised in the reduction step (process variant (1) above), the former in solution in a polar protic solvent such as an alcohol for example methanol or ethanol, and the solid form suspended in a suitable medium such as a polar protic solvent, for example methanol.

It will be appreciated that compounds of formula III and IV exist in E- and Z-isomers about the imine bond, and such isomers are also included in the present invention.

In the above process variant (1), reduction can be performed in the polar protic solvent, referred to above, utilising a hydride reducing agent, such as for example sodium borohydride, sodium cyanoborohydride or hydrogen over palladium/charcoal, preferably at a temperature of from 0° C. to 50° C. Alternatively reduction can be carried out with lithium aluminium hydride in tetrahydrofuran or ether.

Novel intermediates of formula III and IV above can be produced by reacting a tetra-aldehyde of formula:

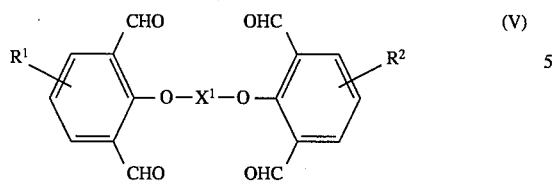

where $X^1$ is X and Y, with appropriate amines such as for example

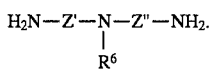

Compounds in which $R^3$ and $R^4$ are different from $R^1$ and $R^2$ can be prepared by reacting a mixture of the compound of formula V above with the corresponding compound substituted with $R^3$ and $R^4$.

The reaction is preferably carried out using two moles of the tetra-aldehyde with four moles of the amine, in a solvent such as an alcohol. The reaction concentration of tetra-aldehyde V is preferably proportional to approximately 1 g in 5 to 40 ml solvent.

Compounds of formula V can in their turn be prepared from known benzene-1,3-dicarboxaldehydes as for example:

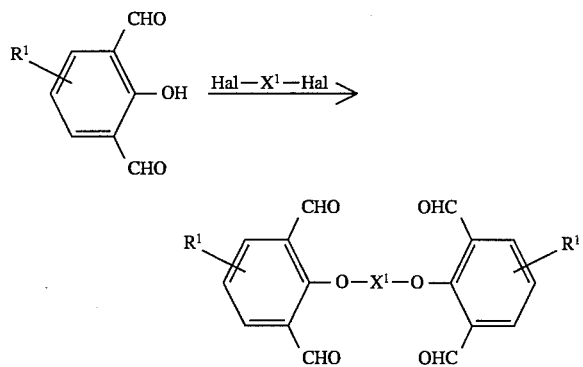

where Hal is chloro, bromo or iodo. When the values of $R^1$ and $R^2$ differ, the tetra-aldehyde can be similarly prepared using equimolar quantities:

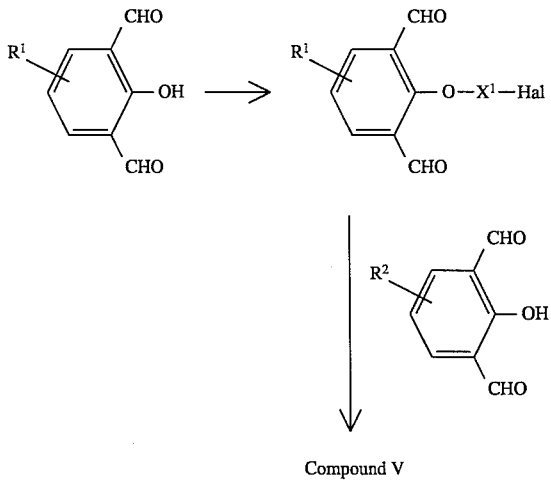

Compound V

The reaction can be carried out in the presence of alkali metal base, for example potassium carbonate, sodium carbonate, sodium hydride or an alkali metal hydroxide in a polar aprotic solvent such as for example dimethylformamide or N-methylpyrrolidone, preferably at a temperature of from 50° C. to 150° C.

With regard to process variant (2) above, a compound of formula I can be alkylated in conventional ways with an alkylating agent of the formula R-Hal where R takes an appropriate value and Hal is chloro, bromo or iodo, preferably in an inert organic solvent and at a temperature of from 0° C. to 100° C. Alternatively, a compound of formula I can be methylated with formaldehyde and formic acid.

As mentioned above, the compounds of formula I in which $R^5$ to $R^{16}$ are hydrogen, have central nervous system activity. For example, the compounds have been found to affect calcium ion uptake into cortical synaptosomes in a test based on that described by McMahon, R. T. and Nicholls, D. A., 1991, J. Neurochem, 56, 86–94. Compounds of the invention inhibit calcium uptake at concentrations of less than 10 μM.

The compounds block the binding of ω-conotoxin GVIA to rat cortical membranes, see Scott R. H. et al., British J. Pharmacol. 106, 199–207. Furthermore compounds are effective as inhibitors of calcium ion current into HEK 293 cells transfected with the human brain N-type voltage sensitive calcium channel (Williams et al., Science 257, 389–395 (1992) at concentrations of less than 10 μM.

The compounds of the invention are indicated for use in the treatment of diseases of the central nervous system. They are of use in the treatment of neurological disorders such as acute neurodegenerative diseases, for example, stroke, cerebal ischemia and head and spinal cord trauma, and chronic neurodegenerative diseases such as, for example, Alzheimer's disease, Parkinson's disease, Amyotrophic lateral sclerosis, AIDS-induced dementia and Huntington's chorea. The compounds are also indicated for use in the treatment of psychotic conditions such as schizophrenia, schizophreniform diseases, acute mania and anxiety, or impairment of learning or memory.

The invention also includes a pharmaceutical composition comprising a pharmaceutically acceptable diluent or carrier in association with a compound of the invention, or a pharmaceutically acceptable salt or ester thereof.

The compounds may be administered by various routes, for example by the oral or rectal route, topically or parenterally, for example by injection or infusion, being usually employed in the form of a pharmaceutical composition. Such compositions are prepared in a manner well known in the pharmaceutical art and comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing, for example, up to 10% by weight of the compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydrobenzoate, talc magnesium stearate and mineral oil. The compositions of an injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the conditions to be treated, the choice of compound to be administered and the chosen route of administration, and therefore the above dosage ranges are not intended to limit the scope of the invention in any way.

As mentioned above, compounds of formula I, and also intermediates of formula III and IV, are chelating agents. They chelate with metal cations, especially transition metal cations, to form metal complexes, and are thus of use in bioinorganic chemistry, materials science, catalysis, separation processes, hydrometallurgy, and in the transport and activation of small molecules.

A particular application is in hydrometallurgical techniques. A leaching process to dissolve metals is first carried out and this is followed by solvent extraction to separate and recover the metal ions of interest. The chelating compounds of the invention have utility in such methods of solvent extraction and are particularly useful in the recovery of copper, in cobalt-nickel separation and in the concentration of uranium.

This invention is illustrated by the following Preparations and Examples.

PREPARATION 1

1,4-Di(2,6-Diformyl-4-Methylphenoxy)Butane

A stirred suspension of 2-hydroxy-4-methylbenzene-1,3-dicarboxaldehyde (2.46 g, 15 mmol), 1,4-dibromobutane (1.51 g, 7 mmol) and anhydrous potassium carbonate (2.21 g, 16 mmol) in dried dimethylformamide (25 ml) was heated to 110° C. for 2 hours under a nitrogen atmosphere. The mixture was allowed to cool to room temperature, water (20 ml) added and the solid product filtered and washed with water. Recrystallisation from dimethylformamide (40 ml) gave the title product as white needles m.p. 205° C.

The following tetra-aldehydes were prepared in a similar manner.

Trans-1,4-di(2,6-diformyl-4-methylphenoxy)but-2-ene m.p. 237° C. using trans-1,4-dichlorobut-2-ene.

1,6-Di(2,6-diformyl-4-methylphenoxy)hexane m.p. 146° C. using 1,6-dibromohexane.

1,4-Di(2,6-diformyl-4-methylphenoxy)phenylene m.p. 244° C. using 1,4-bis(bromomethyl)benzene.

2,6-Di(2,6-diformyl-4-methylphenoxy)naphthylene m.p. 288° C. using 2,6-bis(bromomethyl)naphthalene.

1,4-Di(4-chloro-2,6-diformylphenoxy)butane m.p. 213 20 C. using 5-chloro-2-hydroxybenzene-1,3-dicarboxaldehyde.

1,4-Di(2,6-diformylphenoxy)butane m.p. 190° C. using 2-hydroxybenzene-1,3-dicarboxaldehyde.

1,4-Di(2,6-diformyl-4-methoxyphenoxy)butane m.p. 223° C. using 5-methoxy-2-hydroxybenzene-1,3-dicarboxaldehyde.

EXAMPLE 1

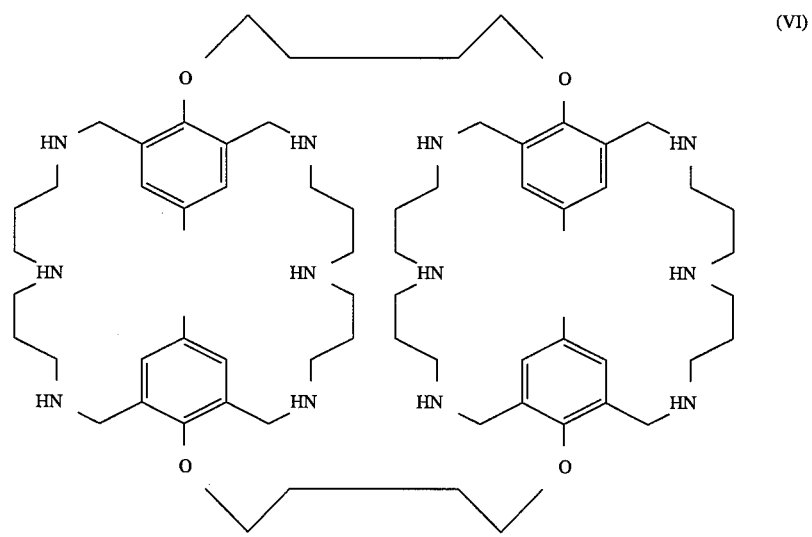

(VI)

Method 1

A suspension of 1,4-di(2,6-diformyl-4-methylphenoxy)butane (1.03 g, 2.7 mmol) and bis(3-aminopropyl)amine (0.71 g, 5.4 mmol) in ethanol (10 ml) was stirred at room temperature for 2 hours under nitrogen. The mixture was heated under reflux for 10 minutes, then stirred overnight at room temperature. Traces of insoluble material (0.08 g) were filtered and the filtrate reduced in volume to approximately 3 ml. A white solid imine crystallised after several days and was filtered (MS MH$^+$ 1146, m.p. 208° C.)

Solid sodium borohydride (0.15 g, 4 mmol) was added portionwise to a stirred solution of the imine (0.50 g, 0.44 mmol) in methanol (10 ml) at room temperature under nitrogen. After 20 hours the mixture was evaporated, water (30 ml) added and extracted with dichloromethane (50 ml). The extracts were dried, filtered and evaporated to a white solid. Recrystallisation from toluene (20 ml) gave white crystals of the product VI (m.p. 165° C.)

Method 2

A stirred suspension of 1,4-di(2,6-diformyl-4-methylphenoxy)butane (6.88 g, 18 mmol) and bis(3-aminopropyl)amine (4.7 g, 36 mmol) in methanol (130 ml) was heated under reflux for 2 hours. The reactant dissolved to give an almost clear solution. After cooling to room temperature traces of insoluble material were filtered. Solid sodium borohydride (2.72 g, 72 mmol) was added to the stirred filtrate in three portions over 1 hour at room temperature under nitrogen. The mixture effervesced and became warm ~30° C. After 3 hours at room temperature the mixture was evaporated, water (100 ml) added, and extracted with dichloromethane (2×100 ml). The extracts were dried, filtered and evaporated to give a white solid. Recrystallisation twice from toluene (100 ml) with hot filtration gave the product VI as a white solid (m.p. 166° C.)

EXAMPLE 2

The amine VI (0.58 g, 0.5 mmol) was dissolved in methanol (10 ml). The solution was filtered and to the filtrate was added a solution of ethanolic hydrogen chloride (~3M, 2 ml). An immediate white precipitate formed. The mixture was evaporated and the residue recrystallised from ethanol (16 ml) and water (3 ml) to give VI hydrochloride as a white solid (MS $MH^+$ 1162, m.p. 240° C.)

EXAMPLE 3

The above product VIII (m.p. 147° C.) was prepared from 1,6-di(2,6-diformyl-4-methylphenoxy)hexane via the imine (m.p. 237° C.) using the procedure described in Example 1, Method 1.

EXAMPLE 5

Compound VIII hydrochloride (MS $MH^+$ 1218, m.p. 227° C.) was prepared from VIII using the method described in Example 2.

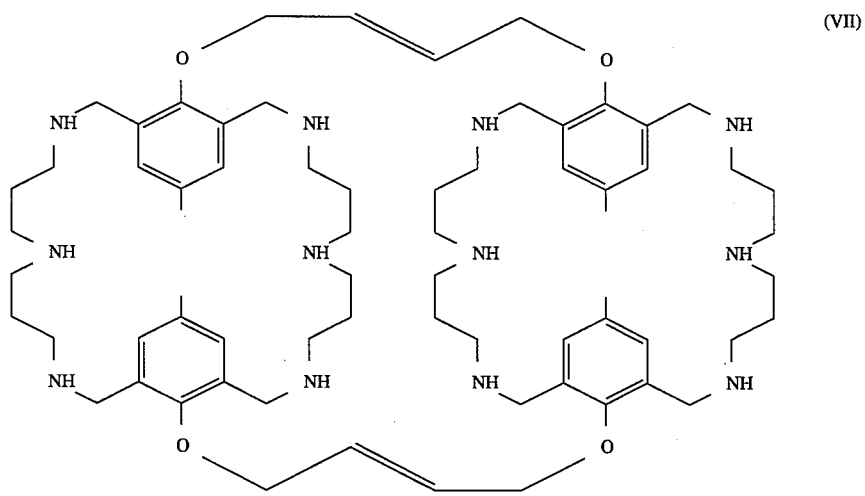

(VII)

The above product VII (MS $MH^+$ 1158, m.p. 146° C. toluene-dichloromethane) was prepared from trans-1,4-di(2,6-diformyl-4-methylphenoxy)but-2-ene using the procedure described in Example 1, Method 2.

EXAMPLE 4

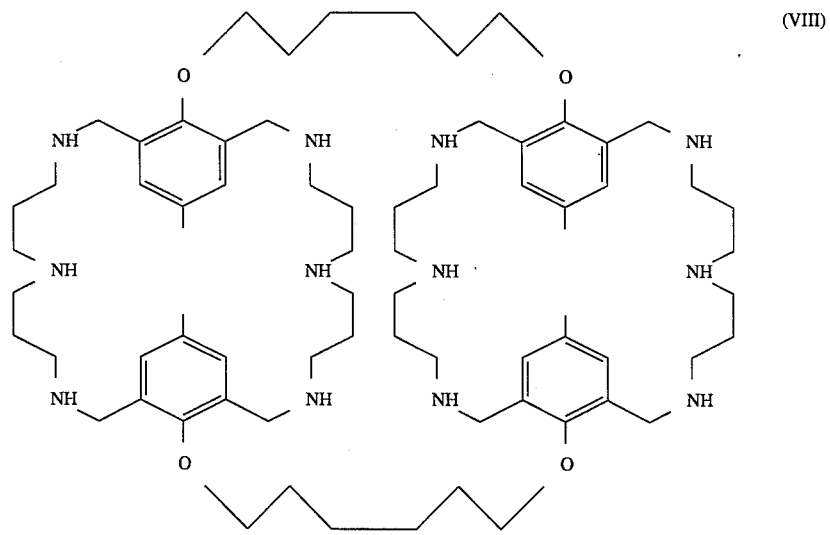

(VIII)

EXAMPLE 6

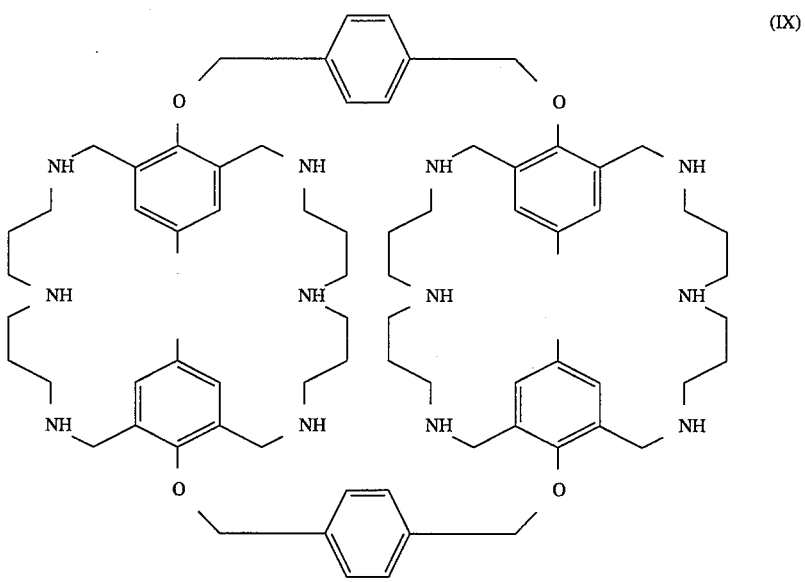

(IX)

Compound IX (m.p. 206° C.) was prepared from 1,4-di(2,6-diformyl-4-methylphenoxy)phenylene by the procedure described in Example 1, Method 1 via the imine (m.p. 255° C.) using a longer heating time of 8 hours at reflux.

EXAMPLE 7

Compound IX hydrochloride (MS MH$^+$ 1258, m.p. 234° C.) was prepared from IX using the method described in Example 2.

EXAMPLE 8

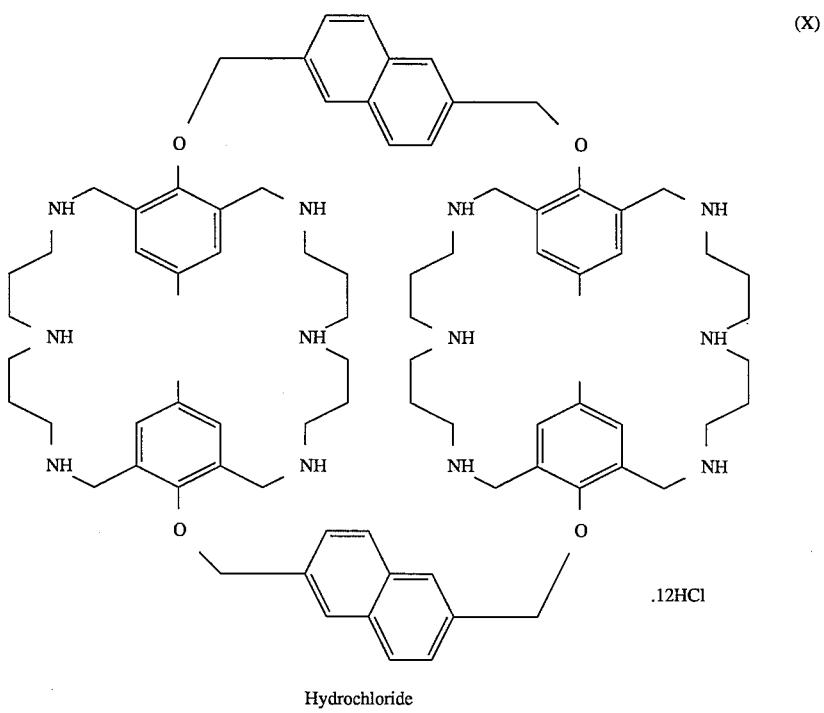

(X)

.12HCl

Hydrochloride

A stirred suspension of 2,6-di(2,6-diformyl-4-methylphenoxy)napthylene (0.96 g, 2 mmol) and bis(3-aminopropyl)amine (0.52 g, 4 mmol) in methanol (40 ml) was heated under reflux for 24 hours. After cooling to room temperature the suspension was filtered to give the imine as a white solid (m.p. 265° C. dec.)

Solid sodium borohydride (0.30 g, 8 mmol) was added portionwise to a stirred suspension of the imine (0.70 g, 0.52 mmol in methanol (30 ml) at room temperature under a nitrogen atmosphere. The mixture was filtered and the filtrate evaporated. To the residue was added water (20 ml) and then extracted with chloroform (2×20 ml). The extracts were dried, filtered and evaporated to give crude X (0.9 g) as an oil. The crude product was dissolved in ethanol (20 ml) and 5M hydrochloric acid (1 ml) added, the hydrochloride salt crystallised as a white solid. Recrystallisation from ethanol (4 ml) water (1 ml) filtering hot and then diluting with hot ethanol (10 ml) gave X hydrochloride as a white solid (MS MH$^+$ 1358, m.p. 240° C.)

EXAMPLE 9

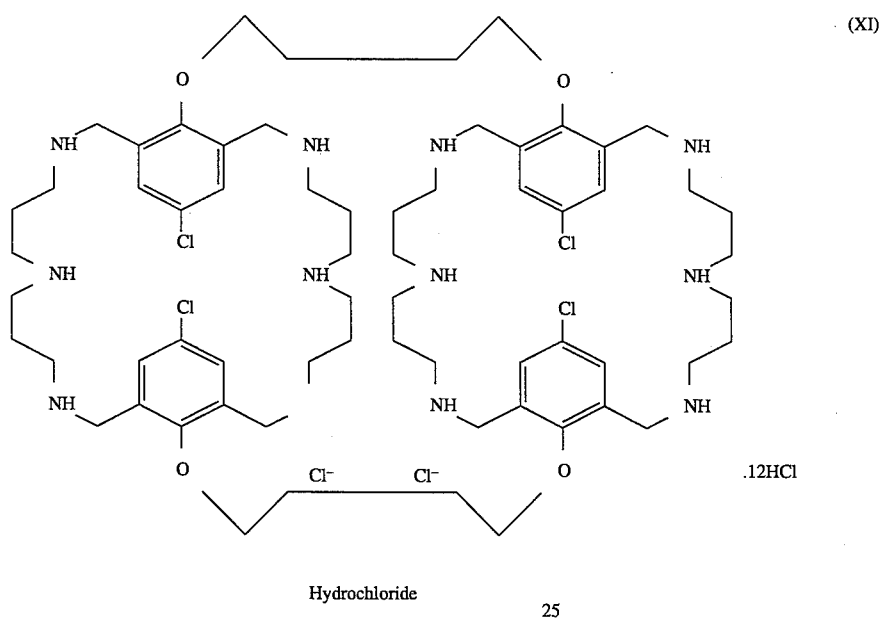

Compound XI was prepared from 1,4-di(4-chloro-2,6-diformyl)butane using the procedure described in Example 1, Method 2. The hydrochloride salt of XI (MS MH$^+$ 1242, m.p. 252° C.) was prepared by the method described in Example 2.

EXAMPLE 10

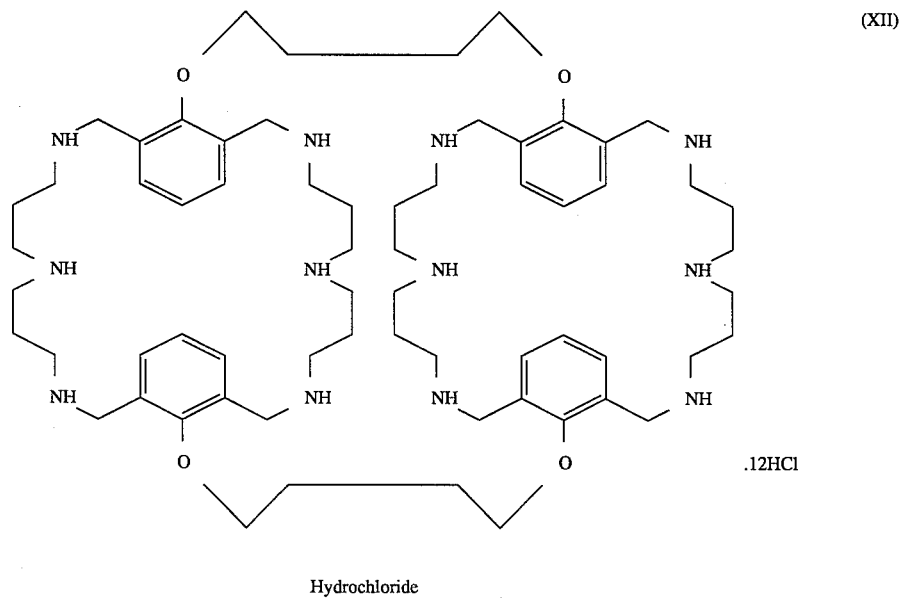

Compound XII was prepared from 1,4-di(2,6-diformylphenoxy)butane using the procedure described in Example 1 Method 2. A sample of the imine was crystallised from methanol-acetonitrile m.p. 158° C. The hydrochloride salt of XII (MS MH$^+$ 1106, m.p. 295° C.) was prepared by the method in Example 2.

EXAMPLE 11

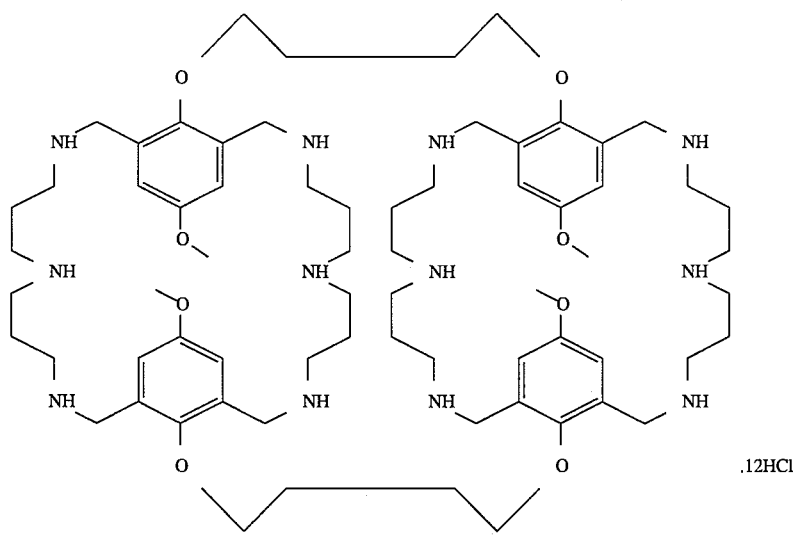

(XIII)

Hydrochloride

Compound XIII (m.p. 171° C.) was prepared from 1,4-di(2,6-diformyl-4-methoxyphenoxy)butane using the procedure described in Example 1, Method 2. A sample of the imine was crystallised from methanol m.p. 240° C. X-ray structure determination of a single crystal of compound XIII (10 mg sample recrystallised from toluene 2 ml) was consistent with the structure drawn. The hydrochloride salt of XIII (MS MH$^+$ 1226, m.p. 278° C.) was prepared by the method described in Example 2.

EXAMPLE 12

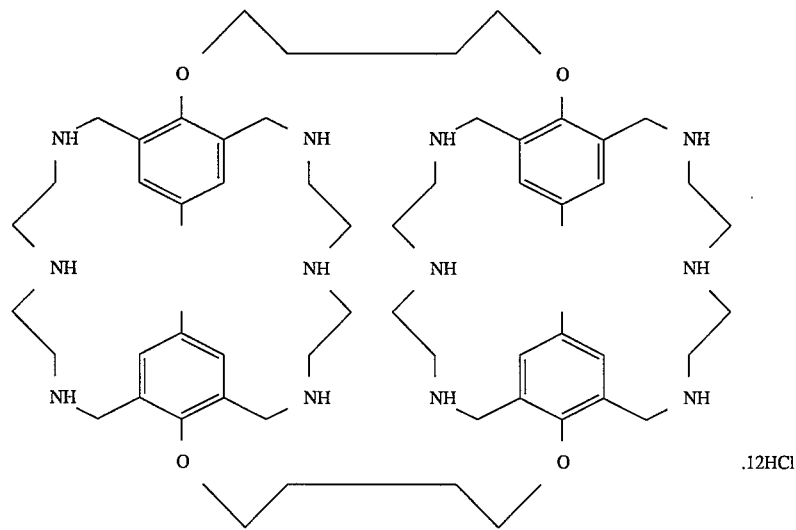

(XIV)

Hydrochloride

The hydrochloride salt of XIV (MS MH$^+$ 1050, m.p. 250° C.) was prepared from 1,4-(2,6-diformyl-4-methylphenoxy)butane and bis(2-aminoethyl)amine using the method described in Example 8. A sample of the imine was crystallised from ethanol m.p. >260° C.

EXAMPLE 13

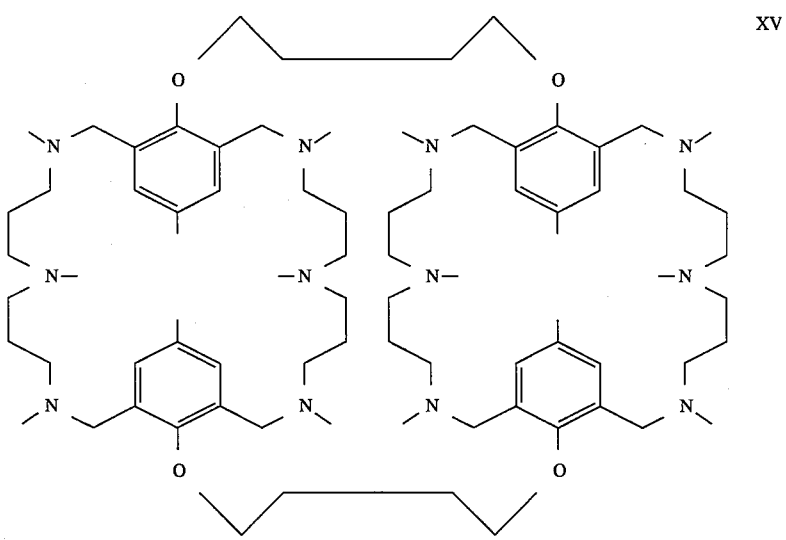

XV

A solution of compound VI (0.35 g, 0.3 mmol) in formic acid (98%, 3 ml) and aqueous formaldehyde (40%, 4 ml) was heated under reflux for 3 hours. The mixture was evaporated and water (20 ml) and 2M sodium hydroxide solution (20 ml) were added. Extraction with chloroform (2×20 ml) gave the crude product as a colourless oil. Crystallisation from acetone (3 ml) gave the product XV as white cubes (MS MH$^+$ 1330, m.p. 117° C.)

EXAMPLE 14

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 15

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

We claim:

1. An intermediate compound of the formula:

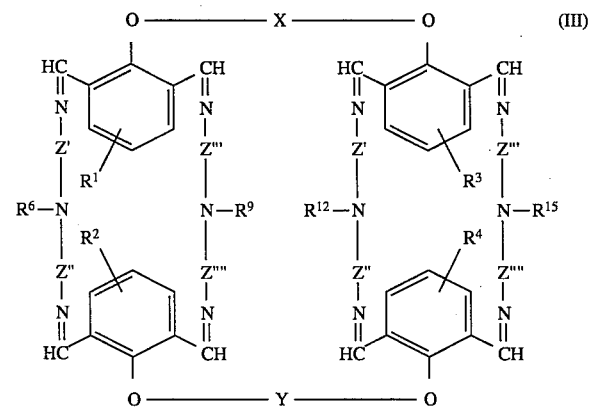

(III)

in which the symbols are as defined in the specification, and salts thereof.

2. An intermediate compound of the formula:

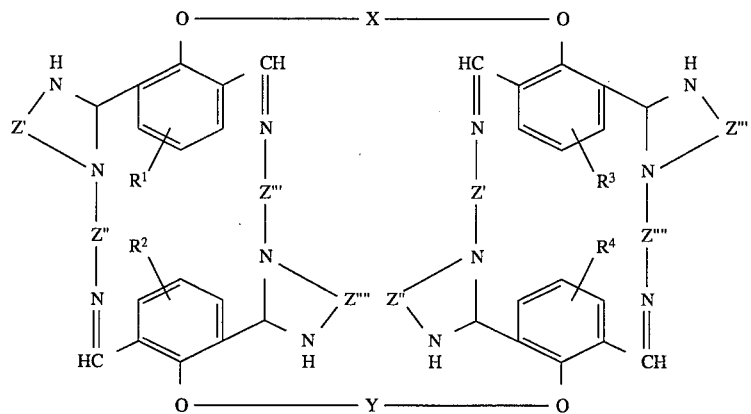 (IV)
in which the symbols are as defined in claim 1, and salts thereof.
* * * * *